(12) United States Patent
Parker

(10) Patent No.: US 11,039,505 B1
(45) Date of Patent: Jun. 15, 2021

(54) METHOD, EQUATION, DESIGN, AND CONSTRUCT TO PROVIDE UNIFORM HEATING FOR THREE-DIMENSIONAL AND VARIOUS SHAPED HEATERS WITH IMPROVED BUSBAR DESIGNS

(71) Applicant: 7788746 Canada Inc., Quebec (CA)

(72) Inventor: Robert Parker, Bend, OR (US)

(73) Assignee: 7788746 Canada, Inc., Laval (CA)

( * ) Notice: Subject to any disclaimer, the term of this patent is extended or adjusted under 35 U.S.C. 154(b) by 0 days.

(21) Appl. No.: 17/078,287

(22) Filed: Oct. 23, 2020

Related U.S. Application Data

(60) Provisional application No. 63/074,138, filed on Sep. 3, 2020, provisional application No. 63/005,745, filed on Apr. 6, 2020.

(51) Int. Cl.
*A42B 3/24* (2006.01)
*H05B 3/06* (2006.01)
*H05B 3/84* (2006.01)
*H05B 3/00* (2006.01)

(52) U.S. Cl.
CPC ............. *H05B 3/84* (2013.01); *A42B 3/245* (2013.01); *H05B 3/0019* (2013.01); *H05B 3/06* (2013.01); *H05B 2203/013* (2013.01); *H05B 2203/016* (2013.01); *H05B 2214/02* (2013.01)

(58) Field of Classification Search
None
See application file for complete search history.

(56) References Cited

U.S. PATENT DOCUMENTS

| | | | |
|---|---|---|---|
| 3,024,341 A | 3/1962 | Ogle | |
| 4,485,927 A | 12/1984 | Corsmeier | |
| 4,656,339 A | 4/1987 | Grise | |
| 4,814,586 A | 3/1989 | Grise | |
| 5,351,339 A * | 10/1994 | Reuber | A42B 3/226 2/15 |
| 5,500,953 A | 3/1996 | Reuber | |
| 8,566,962 B2 * | 10/2013 | Cornelius | A61F 9/028 2/15 |
| 9,419,520 B2 * | 8/2016 | O'Malley | G02B 27/0006 |
| 2008/0264930 A1 * | 10/2008 | Mennechez | H05B 3/84 219/552 |

(Continued)

*Primary Examiner* — Joseph M. Pelham
(74) *Attorney, Agent, or Firm* — Laurence P. Colton; Smith Tempel Blaha LLC

(57) ABSTRACT

A method, equation, system, and device for electrically heating Indium Tin Oxide (ITO) and other transparent conductive materials having a uniform sheet resistivity for defogging and de-icing in a cold environment. The use of nonparallel busbars for connecting the conductive materials reduces excessive and dangerous hot zones. The mathematical analysis and equations provide a means of precisely providing an intermittent electrical connection so that the Watt density and heating is uniform, allowing much higher temperature for de-icing and defogging and more efficient use of energy. This same concept can be used for three dimensional formed heaters to compensate for non uniform sheet resistivity. Also shown are a means of improved busbar designs and an equation and a means of altering sheet resistivity to produce electric heaters with non parallel busbars of various shapes for uniform heating and Watt density.

20 Claims, 8 Drawing Sheets

(56) References Cited

U.S. PATENT DOCUMENTS

| | | | |
|---|---|---|---|
| 2009/0321407 A1* | 12/2009 | Dixon | H05B 3/86 |
| | | | 219/203 |
| 2010/0038356 A1* | 2/2010 | Fukuda | H01C 7/021 |
| | | | 219/549 |
| 2014/0027436 A1* | 1/2014 | Cornelius | G02C 11/08 |
| | | | 219/211 |
| 2014/0374402 A1* | 12/2014 | Cornelius | A61F 9/028 |
| | | | 219/211 |
| 2015/0121610 A1* | 5/2015 | Cornelius | H05B 1/02 |
| | | | 2/435 |
| 2018/0168001 A1* | 6/2018 | Hartzler | H05B 3/34 |
| 2018/0239131 A1* | 8/2018 | Cornelius | H05B 1/0227 |
| 2018/0288830 A1* | 10/2018 | Sajic | H05B 3/145 |
| 2020/0154526 A1* | 5/2020 | Ester | H05K 3/125 |
| 2020/0260532 A1* | 8/2020 | Sajic | H05B 3/36 |

* cited by examiner

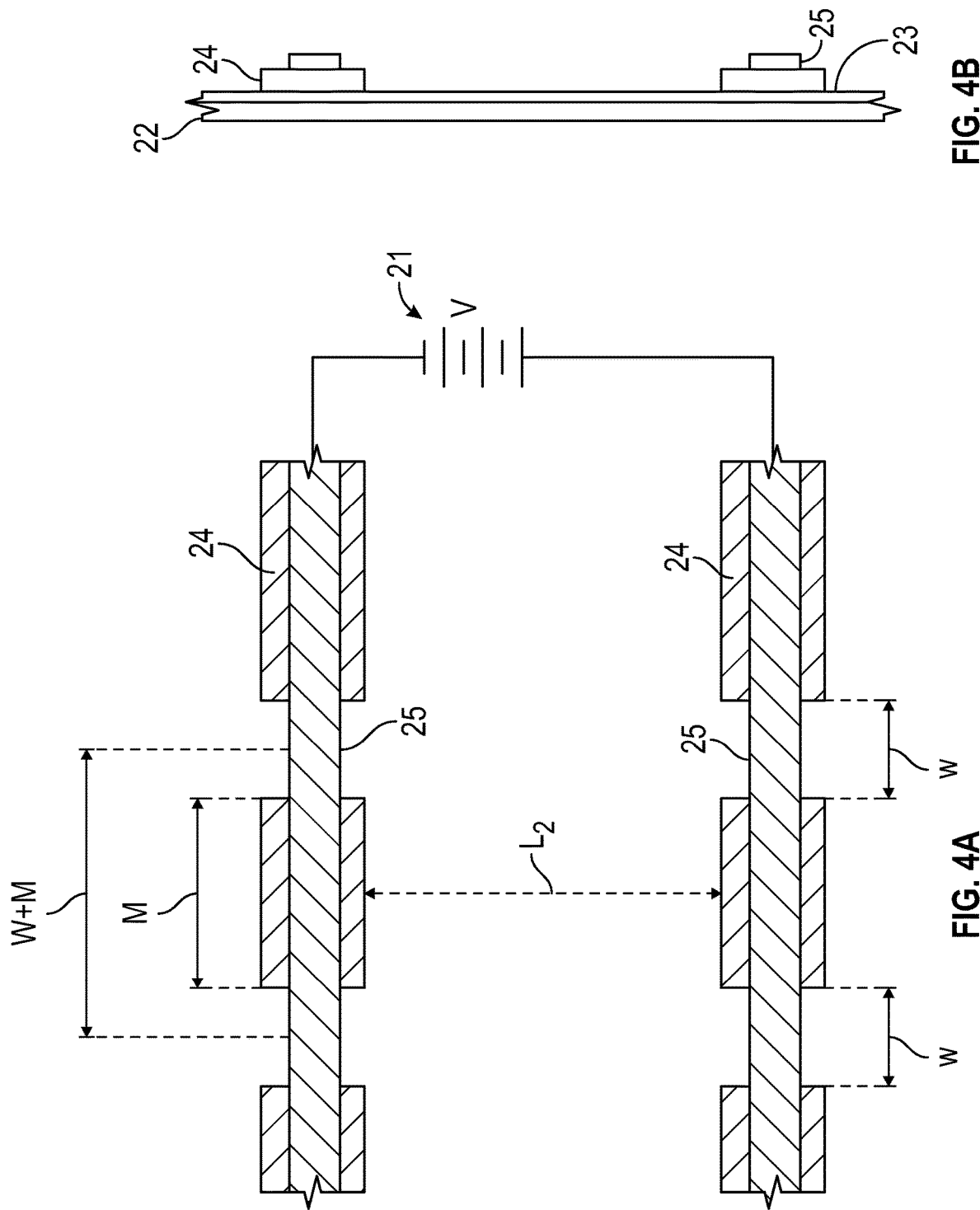

METHOD, EQUATION, DESIGN, AND CONSTRUCT TO PROVIDE UNIFORM HEATING FOR THREE-DIMENSIONAL AND VARIOUS SHAPED HEATERS WITH IMPROVED BUSBAR DESIGNS

STATEMENT OF RELATED APPLICATIONS

This patent application claims the benefit of and priority on U.S. Provisional Patent Application No. 63/074,138 having a filing date of 3 Sep. 2020 and U.S. Provisional Patent Application No. 63/005,745 having a filing date of 6 Apr. 2020, both of which are incorporated herein by this reference.

BACKGROUND OF THE INVENTION

Technical Field

The present disclosure generally is in the field of providing uniform heating for various electric heater shapes. The present disclosure more specifically is in the field of electrically heating transparent conductive materials with a uniform sheet resistivity for defogging and de-icing various surfaces.

Prior Art

Transparent conductive materials have been used to provide transparent heated shield and goggle lenses using ITO (Indium Tin Oxide) as a coating on clear substrates such as polymers. Conductive films using silver nano particles and carbon are available from sources such as Chasm Corporation as alternatives to the ITO. These materials when connected electrically by means of printed silver conductive busbars to a power source can be heated to some design temperature, so that snow, ice, or vapor condensation or fogging can evaporate or melt, thus providing a clear visual window in inclement or high humidity weather. U.S. Pat. Nos. 5,500,953 and 5,351,339 to Reuber and U.S. Pat. No. 3,024,341 and others describe this concept. In addition, U.S. Pat. Nos. 4,485,927, 4,656,339, and 4,814,586 disclose a busbar using continuous stripes of printed silver and an overlay of a continuous copper strip to connect with uniformly printed stripes of printed carbon conductors for use with printed underfloor heaters.

A problem with the prior art mentioned above is that the distance between the printed busbars varies depending on the visual design or design shape. This can lead to non-uniform heating and hotspots in the coating, or overheated areas that can cause burning and distortion in the heated lens coating and/or substrate. This prior art, in addition to causing hotspots and possible distortion, severely limits the use of goggles or visors of this type at extremely low temperatures due to limitations and the glass point of the plastic substrate. The non-uniform heating when charged by a battery source would require larger batteries and would reduce functional operation, such as heating time.

Inclement weather and changes in humidity as well as deep cold provide challenges to users of goggles, visors, spectacles, and other lenses. For example, such weather and humidity changes can cause lenses to fog, allow snow to adhere to, or allow frost or ice to form on such lenses. Coatings which prevent fogging have their limitations and existing systems using a dual paned lens configuration with an ITO sputtered lens with silver bus bars for supplying electrical power to the ITO fail to provide consistent manageable performance. Goggle lenses using ITO and other transparent conductive materials with a uniform sheet resistivity are electrically heated for defogging and de-icing in a cold environment. The design of nonparallel busbars used to connect the conductive material can at room temperature cause excessive and dangerous hot zones on the conductive materials.

What is needed in the art is a method, design, and construct for providing uniform heating to surfaces, such as goggles, using electrically heated conductive films. It is to such methods, designs, and constructs, and others, that preferred embodiments of the present disclosure are directed.

BRIEF SUMMARY OF THE INVENTION

Briefly, a broad aspect of the present disclosure is and relies on a method for uniform heating of surfaces, comprising using continuous conductive busbars and dielectric coatings so as to have an intermittent electrical contact with a conductive film to provide uniform heating. Clear substrates are coated with a uniform transparent conductive film, and a novel busbar arrangement is applied to generally opposite sides of the conductive film so as to provide a more uniform heating of the conductive film over the entirety of the lens.

Another broad aspect of the present disclosure includes a mathematical analysis with developed equations and a means of precisely providing an intermittent electrical connection so that the Watt density to, and heating of, the conductive materials is uniform, allowing much higher temperature for de-icing and defogging and more efficient use of energy. This same concept can be used for three-dimensional formed heaters to compensate for non uniform sheet resistivity.

A further broad aspect of the present disclosure includes a means of yielding improved busbar designs, including an equation and a means of altering sheet resistivity to produce electric heaters with non-parallel busbars of various shapes for uniform heating and Watt density.

Other broad aspects of the present disclosure include methods for uniform heating of surfaces, comprising using conductive busbars and dielectric coatings so as to have an intermittent electrical contact with a conductive film to provide uniform heating.

These representative methods also can include busbars that are continuous.

These representative methods also can include busbars that are not parallel to each other.

These representative methods also can include dielectric coatings that are transparent.

These representative methods also can include conductive films that are transparent.

The above representative methods also can include embodiments in which the non-contact spacing used to provide uniform heating M between busbars is determined by the equation $$M = \left(\frac{L_1}{L_2}\right)^2 w - w,$$

where $L_1$ is the longer path between busbars, $L_2$ is any path between busbars, and W is an electrical contact distance.

All of these representative methods also can include dielectric coatings that are continuous, preventing a continuous busbar over the dielectric coatings from contacting the conductive film except where the busbar protrudes past the dielectric coating making contact.

All of these representative methods also can include electrical busbars that are continuous except where a dielectric coating underneath the busbar prevents electrical contact.

All of these representative methods also can include busbars that are bonded with a conductive adhesive to a thin copper foil and then laminated together.

All of these representative methods also can include the use of a copper foil that is soldered to a power supply.

All of these representative methods also can include using a tapered or decreasing width busbar for uniform resistance heaters.

All of these representative methods also can include constructing intermittent contact busbars for three-dimensional transparent conductive heaters.

Additional broad aspects of the present disclosure, including in connection with all of the previously mentioned representative methods, include methods of using varying sheet resistivity to provide uniform heating for heaters without parallel busbars.

All of these representative methods also can include determining the sheet resistivity using the equation $$\rho_2 = \rho_1 \left(\frac{L_1}{L_2}\right)^2$$

for uniform heating.

All of these representative methods also can include using voids or holes in the conductive heater material to increase sheet resistivity.

All of these representative methods also can include using conductive dots on the conductive heater material to decrease sheet resistivity.

All of these representative methods also can include using a combination of conductive dots and voids to give a wide variation of sheet resistivity.

All of these representative methods also can include providing non-uniform heating with parallel busbar heaters.

Further broad aspects of the present disclosure include devices and machines for manufacturing the three-dimensional busbars taught in this disclosure. Representative embodiments of such a device for manufacturing three-dimensional busbars include a device for manufacturing three-dimensional busbars on a three-dimensional substrate for use as a three dimensional heater, the device including means for constructing intermittent contact busbars on the three-dimensional substrate, wherein the three-dimensional heater comprises the busbars, which are electrically conductive, and dielectric coatings so as to have an intermittent electrical contact with a conductive film on the surface of the three-dimensional substrate, thereby providing uniform heating of the three-dimensional substrate suing the three dimensional heater.

Similarly, further broad aspects of the present disclosure include using the methods and/or devices and machines disclosed herein to produce apparatuses such as goggles and visors, as well as the goggles and visors produced thereby. Such methods of use can be accomplished using any of the representative methods, devices, and/or machines disclosed herein, or combinations of any of the representative methods, devices, and/or machines disclosed herein. Likewise, such apparatuses can be produced or otherwise made or manufactured using any of the representative methods, devices, and/or machines disclosed herein, or combinations of any of the representative methods, devices, and/or machines disclosed herein. As used in this disclosure, the terms "goggles" and "visors" are used as representative terms for all appropriate eyewear and eye coverings, including, but not limited to, goggles, visors, eyeglasses, face screens, face masks, eye masks, lenses, and the like.

Similarly, further broad aspects of the present disclosure include using the methods and/or devices and machines disclosed herein to produce apparatuses such as transparent shields, as well as the shields produced thereby. Such methods of use can be accomplished using any of the representative methods, devices, and/or machines disclosed herein, or combinations of any of the representative methods, devices, and/or machines disclosed herein. Likewise, such apparatuses can be produced or otherwise made or manufactured using any of the representative methods, devices, and/or machines disclosed herein, or combinations of any of the representative methods, devices, and/or machines disclosed herein. As used in this disclosure, the term "shield" is used as a representative term for all appropriate transparent and heated barriers, including, but not limited to, windshields, car windows, windows for buildings, windows for refrigerated storage rooms, etcetera.

Similarly, further broad aspects of the present disclosure include using the methods and/or devices and machines disclosed herein to produce apparatuses such as mirrors (where a reflective layer may be added to the substrate providing shape to the mirror), as well as the mirrors produced thereby. Such methods of use can be accomplished using any of the representative methods, devices, and/or machines disclosed herein, or combinations of any of the representative methods, devices, and/or machines disclosed herein. Likewise, such apparatuses can be produced or otherwise made or manufactured using any of the representative methods, devices, and/or machines disclosed herein, or combinations of any of the representative methods, devices, and/or machines disclosed herein.

Another broad aspect is a system for providing uniform heating across a transparent or mirrored surface of non-uniform width. The system includes a base substrate defining a shape of the surface, a thin conductive material applied to the base substrate, busbars applied to the thin conductive material, wherein a first busbar of the busbars is applied to or next to a first edge of the surface and a second busbar of the busbars is applied to or next to a second edge of the surface opposite the first edge, and wherein uniform heating is achieved through one of: a dielectric material positioned between the busbars and thin conductive material to enable intermittent contact between the busbars and the thin conductive material; and at least one of holes, voids and dots applied to the thin conductive material to alter resistivity across a surface defined by the thin conductive material, wherein more of the at least one of holes, voids and dots are present when the busbars are closer together than when the busbars are farther apart. The system may be included in a heated lens. The system may be included in a heated shield.

In the present disclosure, the viewing area of the goggles or visor preferably has a ΔT of 25° C. relative to the ambient temperature so as to melt any snow or frost on the goggle or visor, but in prior art, the smaller area of the goggles above the user's nose may have a ΔT of 100° C. or more, which could damage the goggles or visor coating and/or substrate. Such a large ΔT also means that if the energy is supplied from a battery source, then the goggles or visor will require larger batteries and/or provide less uninterrupted heating time. In addition, prior art conductive silver busbars must be large enough to prevent energy loss and therefore will limit the size of the viewing area. Even with ½" wide silver busbars at the top and bottom of the visor, such as used in prior art helmet shields, 30 to 40% of the energy is lost in the heating of the busbars depending on sheet resistance or conductivity of the transparent conductor. In addition, a mechanical electric connection of the wires from the power source to the busbars using a rivet causes hot spots at the connection and is not as secure as soldered copper or other fastener options, which would be a more robust connection for skiing, snowmobiling, or other activities which involve significant vibration. In addition, the rivet connection Is expensive and time consuming. These and other design flaws will be solved by the following designs.

This summary is provided to introduce a selection of concepts that are further described below in the detailed description. This summary is not intended to identify key or essential features of the claimed subject matter, nor is it intended to be used as an aid in limiting the scope of the claimed subject matter.

These features, and other features and advantages of the present invention will become more apparent to those of ordinary skill in the relevant art when the following detailed description of the preferred embodiments is read in conjunction with the appended drawings in which like reference numerals represent like components throughout the several views

BRIEF DESCRIPTION OF THE DRAWINGS

The features and advantages of the invention will become apparent from the following description taken in connection with the accompanying drawings in which:

FIG. 4A is a front view schematic of and derivation of dielectric spacing and electric contact spacing to have uniform heating of the present teachings;

FIG. 4B is a side view schematic of the derivation of FIG. 4A of dielectric spacing and electric contact spacing to have uniform heating of the present teachings;

DETAILED DESCRIPTION OF PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the spirit and scope of the invention as defined by the appended claims.

Figure 1:
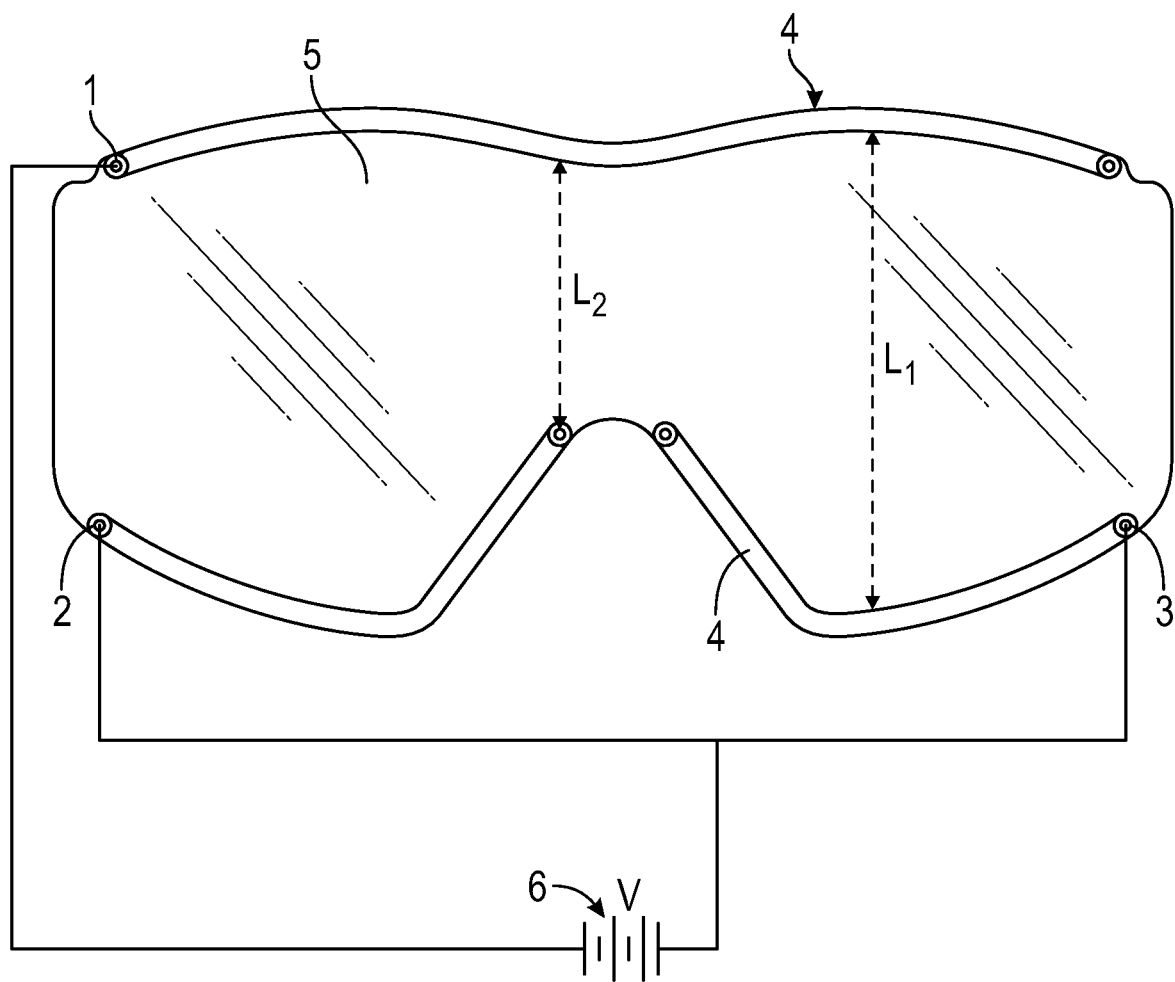
FIG. 1 is a schematic of existing ITO lens and connections used for defogging goggles and visors.

FIG. 1 shows an existing design of a lens for heated goggles. A uniform coating 5 of conductive material on a polymer film is shown on the lens. Typically, Indium Tin Oxide (ITO) is used as the coating 5. However, other transparent conductive materials can be used as the coating, such as, but not limited to, other transparent conducting oxides (TCO), graphene, carbon nanotubes, and poly(3,4-ethylenedioxythiophene) polystyrene sulfonate (PEDOT: PSS), to name a few. The lens substrate may be a clear material, such as, but not limited to, polymer, glass, or ceramic, to name a few.

The coating 5 may have a range of sheet resistivity of 10-60 Ohm/$\square$, and preferably 10-45 Ohm/$\square$, preferably using a 10-12-volt power source. The more conductive the conductive material, the lower the power voltage source needed. For the exemplary embodiments disclosed herein, the coating 5 is applied to the lens substrate using a suitable technique, such as, but not limited to, sputtering, chemical vapor deposition, and sol-gel, to name a few.

Conductive silver busbars 4 are applied along the top of the lens and along the bottom of the lens for providing electrical power to the coating 5. The busbars 4 are printed using an ink with a typical resistivity of 0.15 Ohms/☐. Note that in this innovative design the lower bus bar 4 is discontinuous, therefore requiring multiple electrical connections between the busbar(s) 4 and the power source 6. For example, three electrical connections 1, 2, 3 are shown in the example embodiment of FIG. 1, one to the single top busbar 4, and one each to the two lower busbars 4. Some type of wiring is required from the power source 6 to the busbars 4, using rivets to attach wires. Some designs use a continuous uniform width of busbars 4, that attach to some power source 6 or battery. The busbars 4 can be applied to the lens substrate using a suitable technique, such as, but not limited to, printing, silk-screening, and using an inkjet type of printer, to name a few.

In the exemplary lens of FIG. 1, power, typically from a battery or other similar power source 6, is applied to the busbars 4. This power is conducted across the uniform coating 5 of conductive material and therefore across the lens, causing the coating 5 to heat up, therefore defogging or de-icing the lens. The power source 6 can be any suitable power source, such as, but not limited to, batteries, solar cells, and from an engine or battery of a snowmobile or other machine, to name a few.

In a typical prior art goggle or lens, the distance $L_x$ between the upper busbar 4 and the lower busbar 4 bar varies depending on the design. For example, as shown in FIG. 1 for a common lens design, the distance $L_2$ is about one-half the distance $L_1$. This can lead to an extremely high temperature in the $L_2$ zone—hot enough at room temperature to be extremely uncomfortable to the touch and produce distortion and wasted energy. This high non-uniform temperature would require a bulky expensive battery adding cost to the product.

Figure 2:
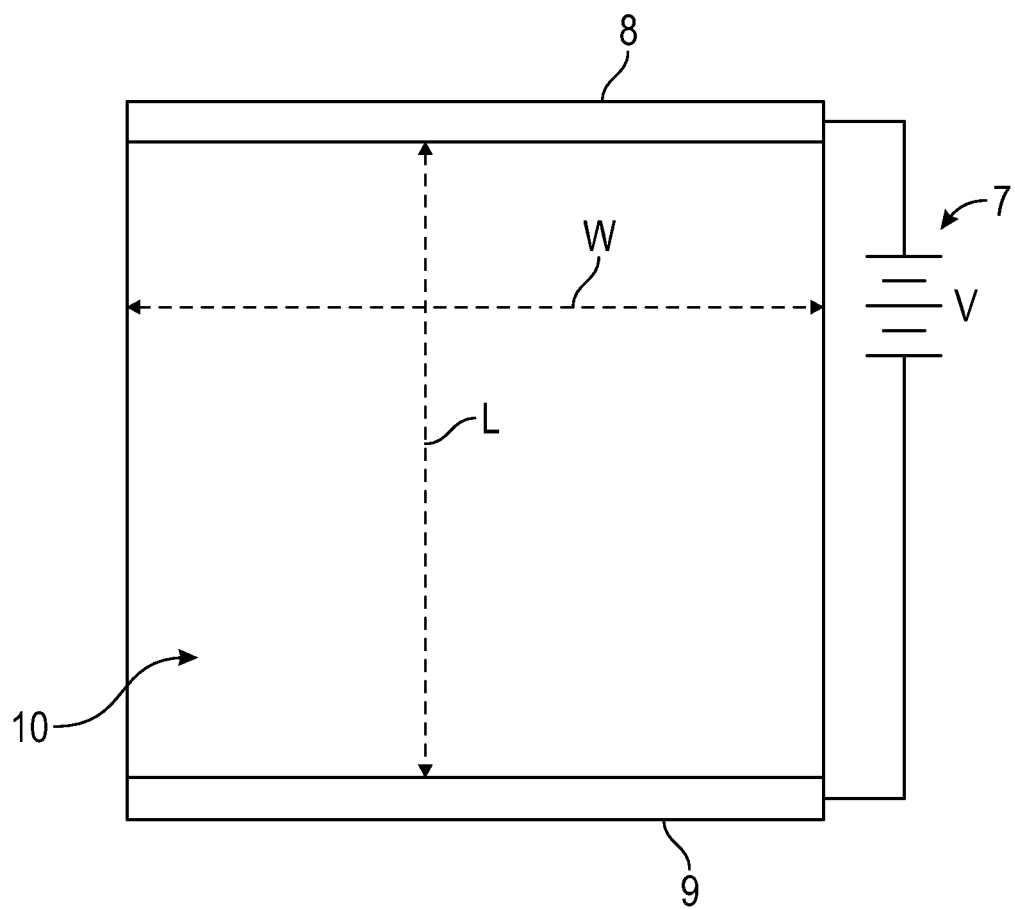
FIG. 2 is a schematic of and derivations of Watt density for parallel busbars separated by distance L.

FIG. 2 is a generalized schematic showing the theory behind the heating of a coating 5 using busbars 8, 9, the coating 5 being a uniform conductive material 10 on a lens. In this schematic, the busbars 8, 9 are formed on a lens or other surface having a width W and are separated by some distance L. The resistance R to the applied voltage (V) is $$R = \rho \frac{L}{W}$$

where L is the length between busbars 8 and 9, and ρ is the sheet resistance of the coating 5 in Ohms/☐. The power in Watts is $I^2R$ where I is the current amps. As $$I = \frac{V}{R},$$

the power $$P = \left(\frac{V}{R}\right)^2 \rho = \frac{V^2 W}{\rho L}.$$

The power density is $$P = \frac{V^2 W}{\rho L(WL)}$$

where (WL) is the area so the power density is $$P = \frac{V^2}{\rho L^2}$$

or Watts/☐. Depending on the free convection constant K, it can be said that the ΔT the temperature rise equation is $$\Delta T = K \frac{V^2}{\rho L^2}. \qquad \text{equation (1)}$$

Based on the above, it can be seen that in FIG. 1 where $L_2$ is approximately one-half of $L_1$, the temperature rise ΔT of the uniform conductive material 10 when power is applied between the busbars 8, 9 and across the uniform conductive material 10 will be four times greater than when $L_2$ is equal to $L_1$. This can severely limit the function of the goggles if, for example, it is snowing at −20° C. or lower. The viewing area $L_1$ preferably has a ΔT=25° C. so as to melt the snow, but if $L_2$ is approximately one-half of $L_1$, $L_2$ would have a ΔT=100° C., which at room temperature could distort or destroy the goggles. A range for ΔT can be from about 10° C. to about 40° C. such that the temperature of the goggles is brought up to an actual temperature sufficient to defog/deice the goggles. More specifically, the ΔT should be sufficient to bring the temperature of the goggles to an actual temperature sufficient to defog/deice the goggles.

Figure 3D:
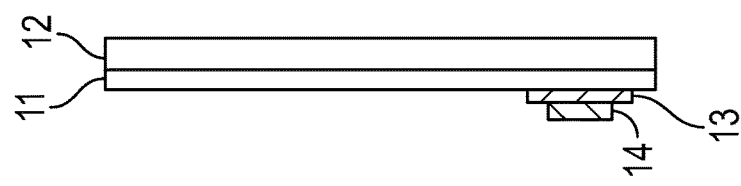
FIG. 3D is a side view of the second method of FIG. 3C of providing intermittent electrical connection with transparent conductive film using clear dielectric printed elements and continuous printed (silk-screened) silver busbars incorporating the present teachings.
Figure 3C:
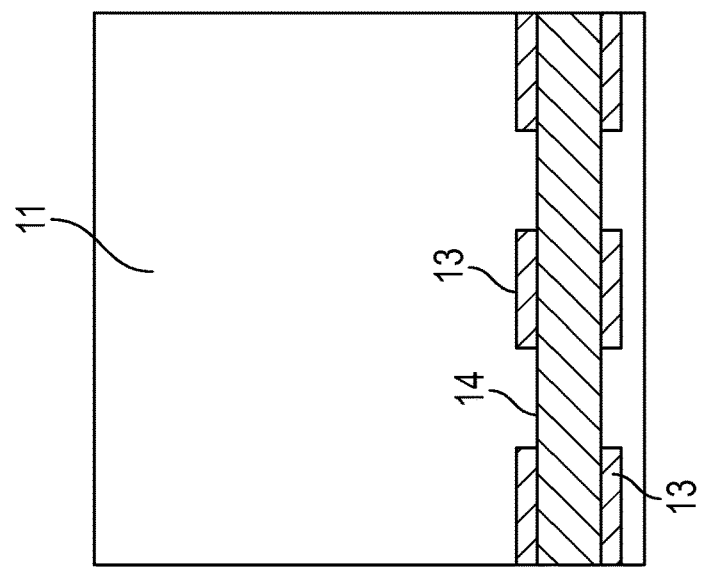
FIG. 3C is a front view of a second method of providing intermittent electrical connection with transparent conductive film using clear dielectric printed elements and continuous printed (silk-screened) silver busbars incorporating the present teachings.
Figure 3B:
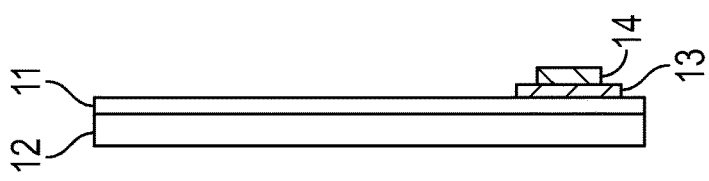
FIG. 3B is a side view of the first method of FIG. 3A of providing intermittent electrical connection with transparent conductive film using clear dielectric printed elements and continuous printed (silk-screened) silver busbars incorporating the present teachings.
Figure 3A:
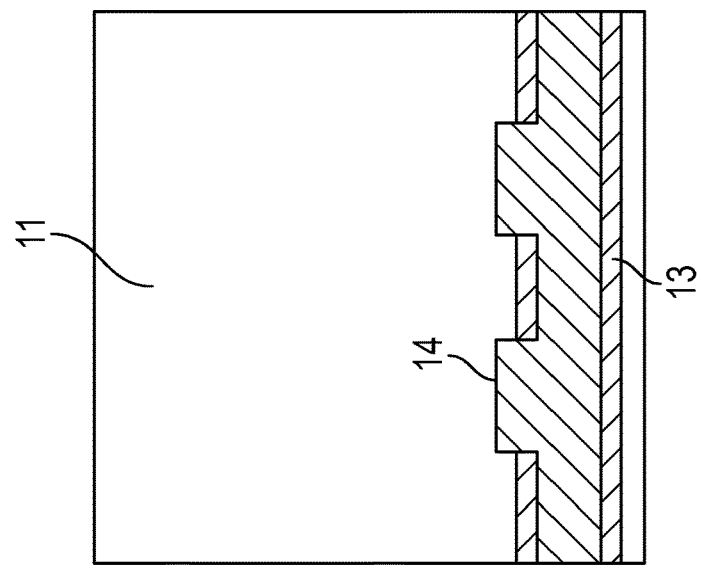
FIG. 3A is a front view of a first method of providing intermittent electrical connection with transparent conductive film using clear dielectric printed elements and continuous printed (silk-screened) silver busbars incorporating the present teachings.

To avoid these problems, the present teachings contemplate providing an intermittent electrical contact with a transparent dielectric material 13 while still providing a continuous bus bar 4 as shown in FIGS. 3A and 3B.

FIG. 3A is a front view and FIG. 3B is a side view of a first method of providing intermittent electrical connection with a transparent conductive film 11 using clear dielectric material 13 as printed elements and printed (silk-screened) silver busbars 14 incorporating the present teachings. More specifically, FIGS. 3A and 3B show a continuous clear dielectric material 13 printed on the conductive material 11, which is ITO deposited on some optically clear polymer film 12. A continuous layer of silver conductive busbar 4 is printed with a small segment of busbar 14 extending over the dielectric material 13 and making electrical contact with the ITO. In the example shown in FIGS. 3A and 3B, the base is polymer 12. Completely coating the polymer 12 base is the conductive material 11. Next, the dielectric material 13 is coated over the conductive material 11. As shown, the dielectric material 13 is a continuous strip on the conductive material 11 over the entire width from left to right in FIG. 3A. Next is the silver busbar 14 on top of the dielectric material 13, silver busbar 4 being entirely on top of the dielectric material 13 and not touching the conductive material 11 except for the small segments of busbar 14 touching the conductive material 11 as shown in FIGS. 3A and 3B. The layers of construction of this first method are shown in the side view of FIG. 3B.

FIG. 3C is a front view and FIG. 3D is a side view of a second method of providing intermittent electrical connection with a transparent conductive film 11 using clear dielectric material 13 as printed elements and printed (silk-screened) silver busbars 4 incorporating the present teachings. More specifically, FIGS. 3C and 3D show an alternate and preferred way of making intermittent contact, as this structure uses less dielectric material 13 and less silver busbar 4, 14 material than, for example, the method shown in FIGS. 3A and 3B. Here, a transparent dielectric material 13 is printed in busbar segment 14 as so to prevent electrical contact of the continuous printed bus bars 4 from making electrical contact with the ITO conductive film 11. The dielectric material 13 is preferably transparent so as to not interfere with the user's vision through the goggles. The dielectric material 13 is shown as discontinuous squares on the conductive material 11 so as to not allow contact between the silver busbar 14 and the conductive material 11. Next is the silver busbar 14 on top of the dielectric material 13 squares and also partially on top of the conductive material 11. The small segments 14 shown in FIGS. 3A and 3B touching the conductive material 11 are generally the equivalent of the areas 14 shown in FIG. 3C that is not on top of the dielectric squares 13 and that is touching the conductive material 11. The layers of construction of this second method are shown in the side view of FIG. 3D.

FIG. 4A is a front view and FIG. 4B is a side view schematic of and derivation of the spacing of the dielectric material 24 and the spacing of the electric contact so as to have uniform heating of the present teachings. The example structure shown in FIGS. 4A and 4B has the same general structure as the structure shown in FIGS. 3C and 3D. FIGS. 4A and 4B show the continuous busbars 25 printed over clear dielectric material 24, connected to a voltage power supply 21, with the busbars having intermittent contact with the conductive material 23 due to the presence of the (squares of the) dielectric material 24. The heating or Watt density $$\frac{V^2}{\rho L_2^2}\left(\frac{W}{W+M}\right) = P.$$

The term $$\left(\frac{W}{W+M}\right)$$

is the percent Watt density from the heated zone W spread over the unheated zone M. It can be said that this average Watt density is equal to the Watt density of the longest and coolest spacing or distance between busbars 25 $L_1^2$ or $$\frac{V^2}{\rho L_1^2}$$

giving us the equation $$\frac{V^2}{\rho L_1^2}\left(\frac{W}{W+M}\right) = \frac{V^2}{\rho L_2^2},$$

which results in $$M = \left(\frac{L1}{L2}\right)^2 W - W \qquad \text{equation (2)}$$

where M is the non-contacting distance (unheated zone) between contacting zones W (heated zone). For the purposes of equation (2), and as shown in the embodiments of FIG. 1 for a common lens and of FIG. 2 for a generalized lens, busbars 4 extend across at least a portion of the top and bottom edges of the lens in an overall horizontal orientation relative to each other (parallel busbars), and distances $L_X$ in general and $L_1$ and $L_2$ in specific extend across the lens between busbars 4 in an overall vertical orientation, with each of distances $L_X$ being parallel to each other in this overall vertical orientation. For busbars 4 not positioned in an overall horizontal position relative to each other (non-parallel busbars), one of ordinary skill in the art would be able to determine the orientation of distances $L_X$ relative to the busbars 4, such as being perpendicular to a center line extending equidistantly between the busbars 4.

Arbitrary selection of some contacting distance of W and for some given distance of L between busbars 4, 25 can determine the non contacting or dielectric insulated distance. For an example of the contact zone W on the lens shown in FIG. 1, a contact zone W of 0.125" can be selected. Note the smaller the contact zone the more uniform the Watt density.

Figure 5:
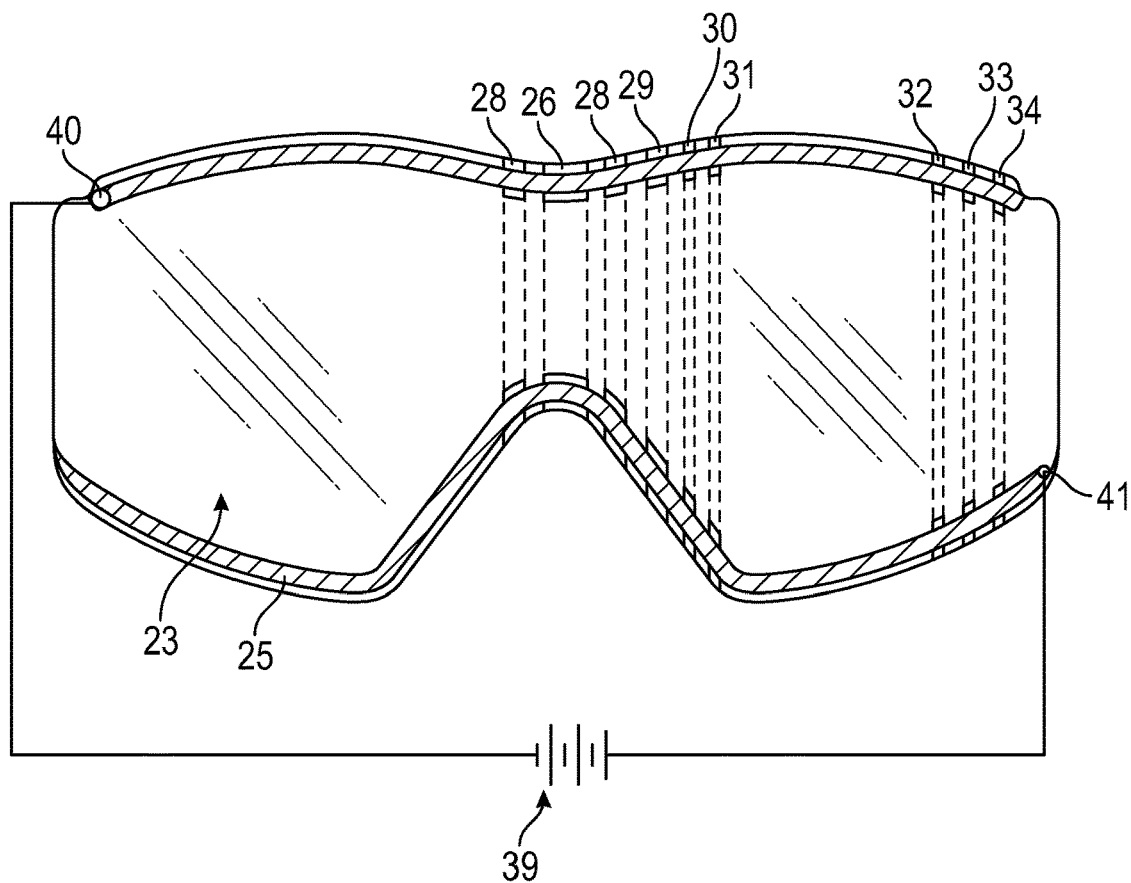
FIG. 5 is a schematic of and computation of dielectric and silver bus bar spacing and contact for defogging of a goggle, visor, or other device incorporating the present teachings.

FIG. 5 is a schematic of and computation of dielectric and silver busbar 4 spacing and contact for defogging of a goggle, visor, or other device or apparatus incorporating the present invention. In FIG. 5, because the left and right parts of the lens are symmetrical, the spacing of non-contact zone M of the dielectric material is placed in the center with the 0.125" contacts. The minimum contact length L is 1.5" and the maximum contact length $L_1$ is 3". Hence $$\left[\left(\frac{L_1}{L}\right)^2 (0.125")\right] - 0.125" = 0.375" = M$$

(for dielectric space 26). Using the same equation, the spacing for dielectric space 28 can be determined. M=0.156" for dielectric space 29; M=0.100" for dielectric space 30; M=0.055" for dielectric space 31; M=0.025" for dielectric space 32; M=0.025" for dielectric space 33; M=0.055" for dielectric space 34; and M=0.100" for dielectric space 35.

The contact zone W is 0.125" and is constant. Also shown in FIG. 5 is where the applied voltage of power source 39 is in contact at connection point 40 and connection point 41, respectively.

The calculation for the dielectric spacing M was performed in the areas of the lens that would have the hottest zones. A prototype was constructed using the dimensions provided above for M and W, was tested, and the lens was essentially uniformly heated. More specifically, the computing of dielectric spacing M, contact spacing W, and silver busbar 4 spacing for defogging of a goggle, visor, or other device as shown in FIG. 5 is provided below. This is constant for the temperature rise ΔT as a function of Watt density. The average temperature across L is relatively uniform, but can vary. The actual temperature across the surface of the lens is not critical as long as the T over the lens is greater than a T that will defog or deice the optical area of the device.

Converting Watt density to ΔT, the conversion is measured as K=0.023 W/0° C./in². If a 25° C. rise or ΔT for the longest distance $L_1$=2" for 45 Ohm/□ ITO is sought, it can be said that $$\frac{V^2}{(2^2) \times 45} = (25).023.$$

$$V = \sqrt{(4)(45)(25).023} = 10.17 \text{ Volts}$$

-continued $$\text{The Watt density} = \frac{V^2}{(2)^2 45} = \frac{10.17}{(4)45} = 0.57^{0.57 Watt}/_{IN^2}$$

Through use of intermittent contacts, which can be referred to as the spaces between the dielectric squares where the silver busbar touches the conductive film, and a uniform Watt density and temperature, the heated area (A) can be multiplied to determine the total Watts of 0.57 Watts/In (A). If this is divided by the voltage, 10.17V, the current can be determined to design the power supply.

Figure 6:
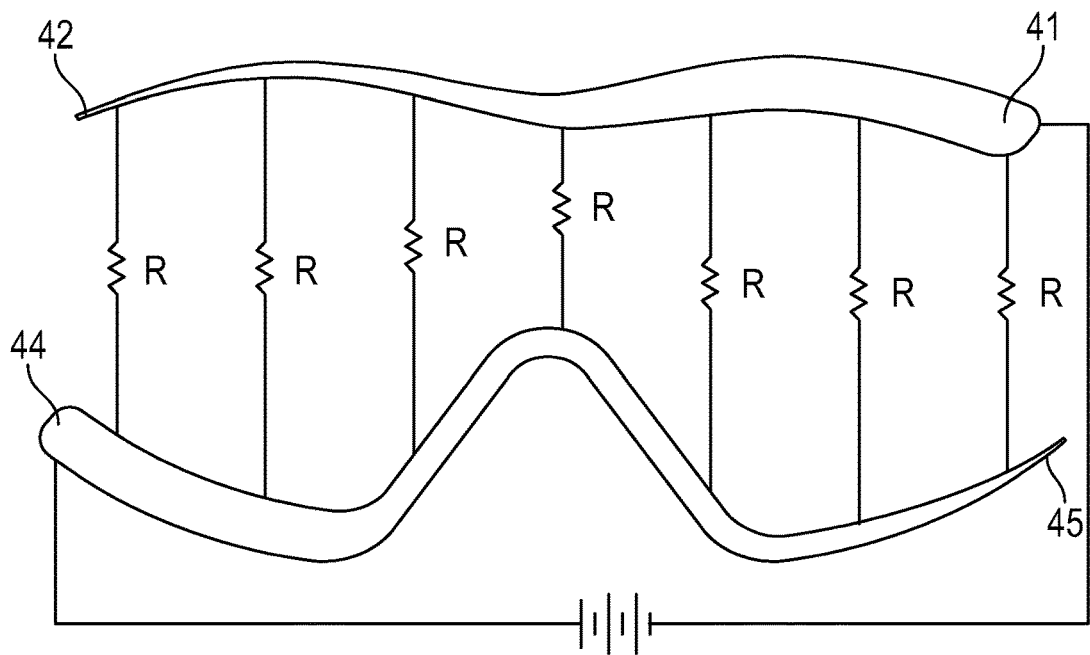
FIG. 6 illustrates the resistance distribution when using tapered busbars for more efficient use of silver and a better viewing area provided by the present teachings.

FIG. 6 illustrates the resistance distribution and tapered busbars 4 for more efficient use of silver and a better viewing area provided by the present teachings. More specifically, FIG. 6 represents the placement of busbars 4 and the various resistances R between the busbars 4 across the lens distance L. Once the intermittent connection and equation (2) is found, uniform resistance R across the busbars 4 is present, as shown in FIG. 6. Although R may vary somewhat across the lens, the average R will be the same across the entire width of the lens, with the Watt density being uniform across the lens. From inspection, it can be seen that the maximum current density is at connection points 42 and 44. The current density is at a minimum at endpoints 41 and 45. So, tapered busbars 4 can be used. This minimizes the amount of printed silver, which saves cost, but more importantly allows for a larger viewing area.

Figure 7A:
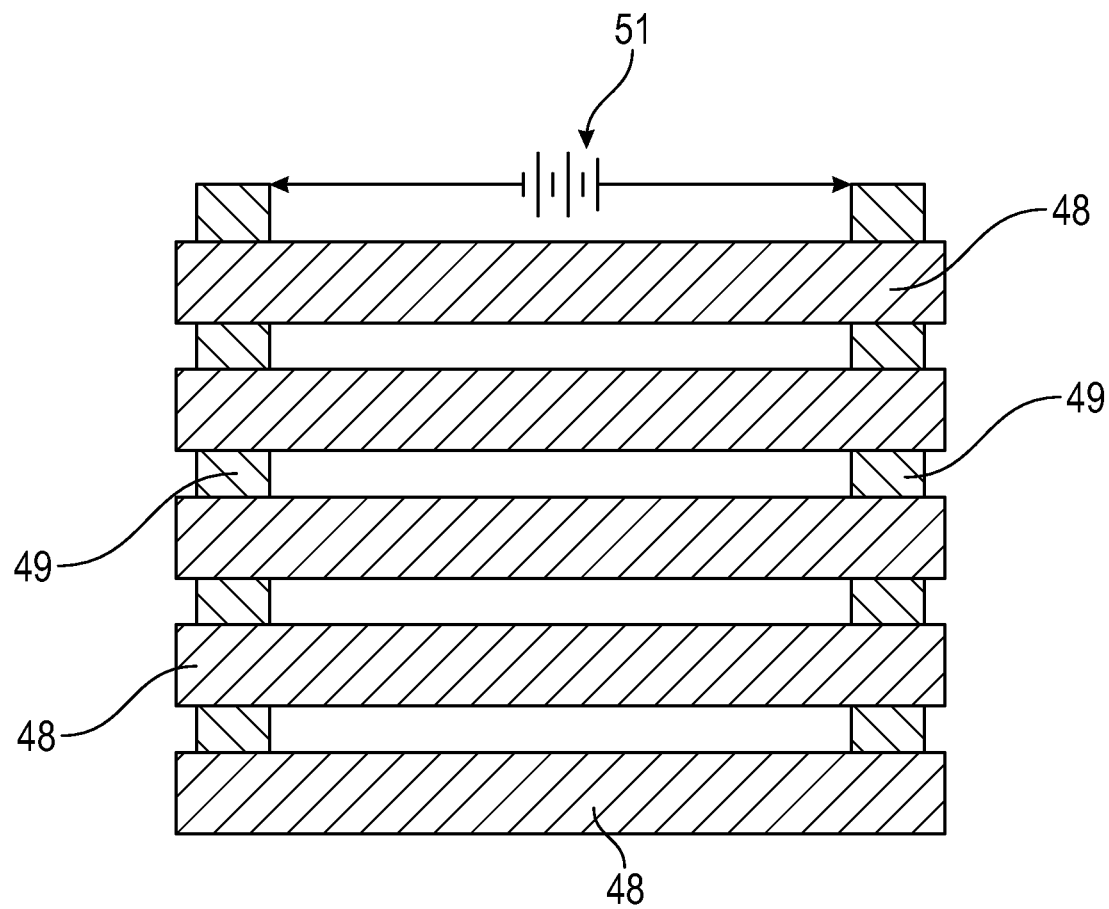
FIG. 7A is a top view schematic of prior art carbon underfloor heaters and busbars.
Figure 7B:
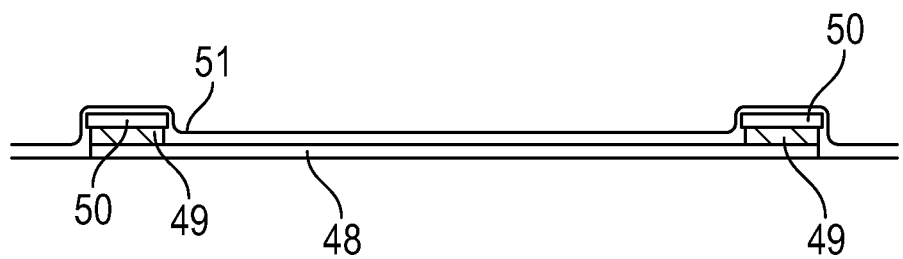
FIG. 7B is a side view schematic of the prior art carbon underfloor heaters and busbars shown in FIG. 7A.

FIG. 7A is a schematic front view of prior art carbon underfloor heater elements 48 and busbars 49, and FIG. 7B is a side view of the prior art device of FIG. 7A. In FIGS. 7A and 7B, drawings of an underfloor heater are shown. Carbon resistive heating elements 48 are printed on a 0.005" polyester film 51. A silver busbar 49 is printed to provide an uninterrupted electrical connection with the heating elements 48. A continuous metal strip about 0.005" thick and 0.5" wide 50 is in contact with the printed silver strip 49 and then adhesively laminated to the coated polyester film 51. In some applications, such as a visor in helmets, large areas are heated using silver busbars 49 as mentioned earlier, and 30% of the energy is lost and a significant part of the viewing area is lost because the busbars 49 are 0.5" wide. A comparison of the sheet resistivity that was computed from the bulk resistance of various metal and printed silvers is:

For 0.001" thick copper, $\rho=0.8\times10^{-3}$ Ohms/□
For 0.001" aluminum, $\rho=1.8\times10^{-3}$ Ohms/□
For 0.001" steel, $\rho=5.5\times10^{-3}$ Ohms/□
For printed silver, $\rho=0.15$ Ohms/□

Clear thin copper is orders of magnitude more conductive than silver. A printed silver busbar only 0.5 mm wide and a copper foil 0.0254 mm thick and 0.5 mm wide bonded together with a conductive adhesive and then laminated with a clear pressure sensitive thin film will be a much more conductive busbar and will also allow for a greater viewing area without Joule heating loss. It will also replace the mechanical contact with a robust secure soldered connection to the voltage source. The difference between the busbar construction in underfloor heaters is the use of much thinner silver/copper busbars, because floor heaters must carry current over meters not centimeters.

Another significant difference in the floor heater, is that the busbars 49 make uninterrupted contact with conductive carbon heating elements 48 as opposed to the teachings of the present disclosure that describes the use of dielectric insulators to provide intermittent contact. 3M sells 0.0014-inch thick copper foil with a conductive adhesive that can be used for the present teachings. Another significant difference is while the floor heater uses continuous strips of metal conductors, due to the design shape the copper foil must be die cut to conform to the lens geometry.

Figure 8A:
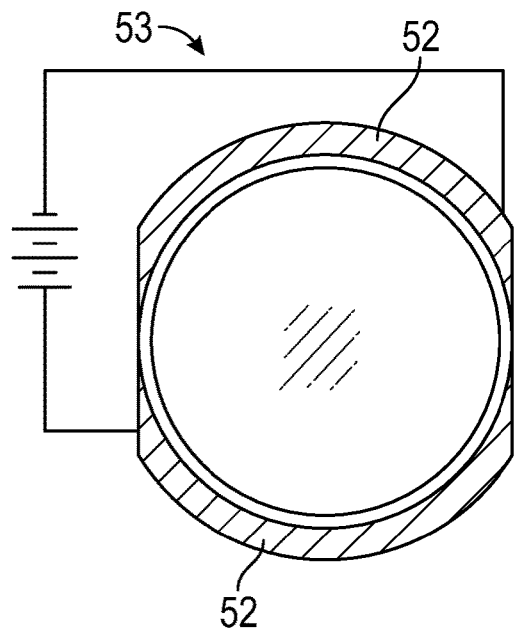
FIG. 8A is a schematic of a front view of a first type of vacuum formed conductive transparent three-dimensional shapes and busbars for defogging using the present teachings.
Figure 8B:
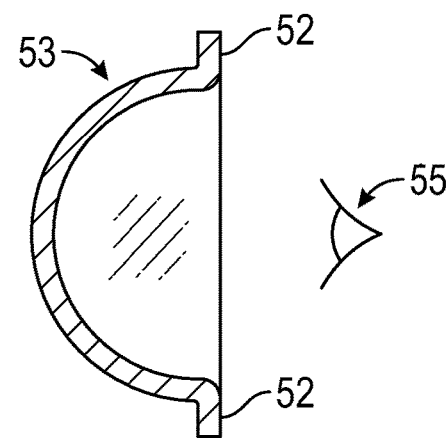
FIG. 8B is a cross-section of the first type of vacuum formed conductive transparent three-dimensional shapes and busbars of FIG. 8A for defogging using the present teachings.
Figure 8C:
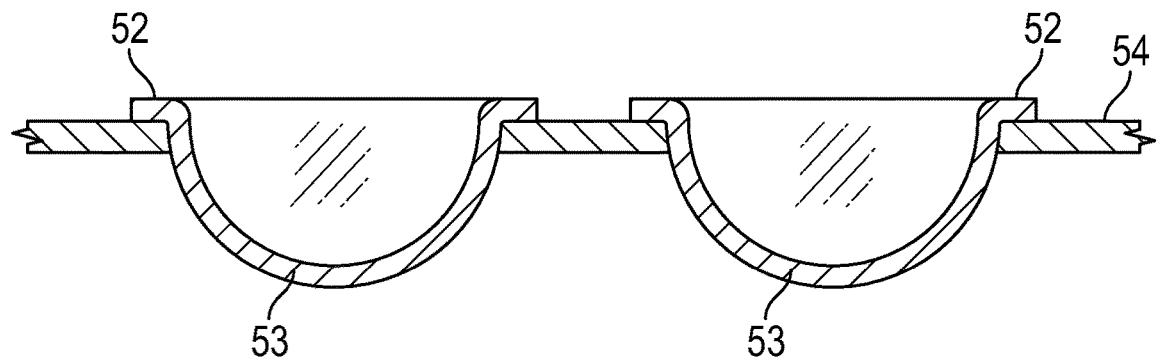
FIG. 8C is a schematic of a top cross-sectional view of a second type of vacuum formed conductive transparent three-dimensional shapes and busbars for defogging using the present method for printing busbars.

FIGS. 8A, 8B, and 8C illustrate embodiments of the present disclosure as applied to three-dimensional shapes, such as rounded goggles 53. FIG. 8A is a schematic of a front view and FIG. 8B is a cross-section of a first type of vacuum formed conductive transparent three-dimensional shape 53 and busbars 52 for defogging using the present teachings. FIG. 8C is a schematic of a top cross-sectional view of a second type of vacuum formed conductive transparent three-dimensional shape 53 and busbars 52 for defogging using the present teachings.

In FIGS. 8A and 8B, a three-dimensional transparent heat formable goggle lens 53 is shown. Transparent films using ITO are impossible to heat form because the ITO is a brittle ceramic. However, Chasm Corporation has developed heat formable transparent conductive films with sheet resistance varying from 10 Ohms/□ to 40 Ohms/□. However, in forming the film, the resistance will vary with the stretched film increasing in resistance. In addition, because of the shape of the surface 53, the distance between busbars 52 will vary giving rise to non uniform heating. To overcome the variable, an intermittent busbar 52 is printed on the flat extended parts of the lens surface 53. The eye of the viewer 55 is shown in FIG. 8B. For example, on the 3D lens shown in FIGS. 8A and 8B, a dielectric may not be necessary towards the middle of the 3D structure, or the spacing of the dielectric may be closer towards the middle and wider towards the sides so that the Watt density across the middle of the 3D lens is the same as across the sides of the lens, as the distance across the 3D shape towards the middle of the lens is greater than the distance across the 3D shape towards the edges of the lens. In FIG. 8C, a fixture 54 (with holes) for holding many lenses is shown to facilitate silk screening silver bus bars simultaneously for many lenses and reduced.

Figure 9A:
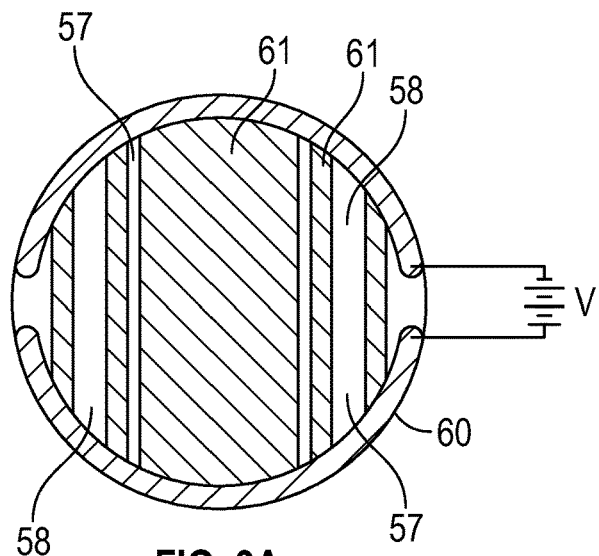
FIG. 9A is a schematic of a first device and method for providing uniform heating with odd shaped heaters using an intermittently spaced carbon conductor and uniform busbars using the present teachings.
Figure 9B:
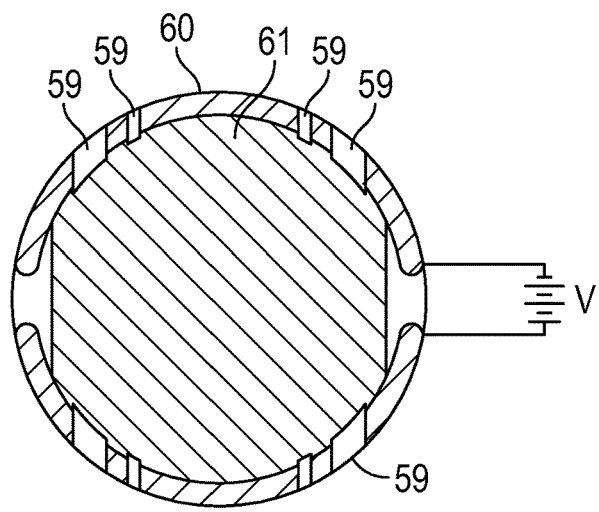
FIG. 9B is a schematic of a second device and method for providing uniform heating with odd shaped heaters using a dielectric and uniform busbars using the present teachings.
Figure 9C:
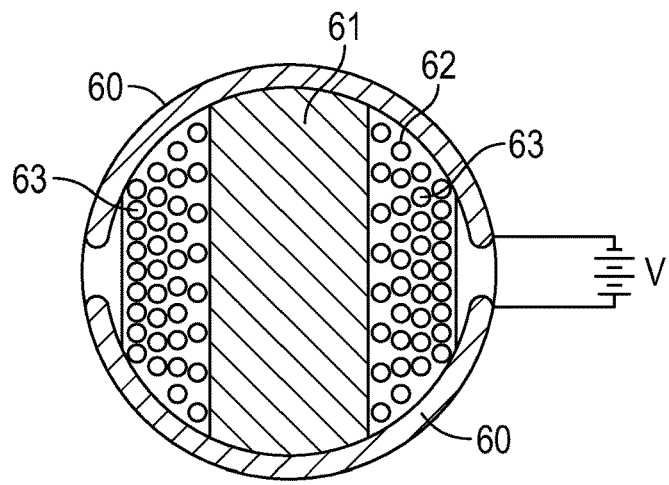
FIG. 9C is a schematic of a third device and method for providing uniform heating with odd shaped heaters using a variable sheet resistance and uniform busbars using the present teachings.

The method disclosed for varying the sheet resistance p to obtain uniform heating with nonparallel busbars can be used to provide non uniform heating. A method for obtaining uniform heating is shown in FIGS. 9A, 9B, and 9C is a circular heater. FIG. 9A is a schematic of a first device and method for providing uniform heating with odd shaped heaters and non uniform busbars using the present teachings. FIG. 9B is a schematic of a second device and method for providing uniform heating with odd shaped heaters and non uniform busbars using the present teachings. FIG. 9C is a schematic of a third device and method for providing uniform heating with odd shaped heaters and non uniform busbars using the present teachings.

In FIG. 9A, areas of a constant sheet resistance are printed on a substrate using uniform conductive material 61. A space 57 is not printed. The spacing between printed segments 61 is determined by equation (2)

$$M = \left(\frac{L1}{L2}\right)^2 W - W.$$

Here again conductive segment 61 is 0.125" wide. The busbar is 60 is 0.125" wide, which will give an approximate uniform heating. Again, if contact zone W is made smaller, the heating will get more uniform.

In FIG. 9B, the formula in equation (2) was again used to provide a dielectric coating to prevent current flow through dielectric coating 59. A uniform constant sheet resistance p is provided for a uniform conductive material 61.

FIG. 9C illustrates a preferred method of obtaining uniform heating by altering the sheet resistivity. Here the sheet resistance is altered as shown in equation (3). If the Watt density of the longest path between busbars 60 and the various paths $L_2$ is set, equation (3) results:

$$\rho_2 = \left(\frac{L_1}{L_2}\right)^2 \rho_1. \tag{3}$$

This means that for any given distance $L_2$, the sheet resistivity $\rho_2$ can be increased so as to obtain uniform heating.

This can be accomplished by having voids 63 in a portion 62 of the conductive material. If one is printing a resistive uniform conductive material 62 so that as L decreases, there are progressively more voids 63 moving from the center of the shown odd shaped heater towards the outer edge of the shown odd shaped heater. In other words, there are fewer voids 63 and/or the voids 63 are spaced further apart (less dense) towards the center of the shown odd shaped heater (that is, closer to the uniform conductive material 61) and there are more voids 63 and/or the voids are spaced closer together (more dense) towards the edges of the odd shaped heater (that is, further from the uniform conductive material 61). This also is true if the conductive medium is a photo etched metal such as Manganin. If the voids 63 are 50% of the area, the sheet resistivity is 50% greater.

If the printed conductor has insufficient conductivity, a series of silver conductive dots can be printed over a carbon conductor, for example, to decrease the sheet resistivity in the longest distance L with decreasing silver dots as $L_2$ gets smaller. One can use a combination of voids 63 in or swiss cheese holes and silver to obtain a wide range of sheet resistivity. Although holes or similar voids 63 are suggested to increase the $\rho$, the sheet resistivity various geometries such as rectangular voids 63 can be used, but small holes or voids 63 are preferred so as to limit hot spots when the current flows around the voids 63. The size of the voids 63 depends on the printing (e.g., silk screening, rotogravure) resolution.

As one of ordinary skill in the art would understand, as the sheet resistivity is altered to obtain uniform Watt density, it becomes a very simple matter to design a complex shape heater. The Watt density is multiplied by the area at the heater to obtain the total Watts.

The present disclosure provides a simple way to design and construct complex shaped heaters for any shape. Many existing heaters use complex long lines of continuous conductive material which results in bends in the shape. Each shape requires a new design and current path. These twists and turns result in nonuniform heating and hot spots. Obviously, this concept greatly improves the design and uniformity.

As one of ordinary skill in the art would understand, it can be said that as the Watt density is constant, the area of the heater can be multiplied by the Watt density to get the total wattage and hence the current so the power supply can be determined.

The various embodiments are provided by way of example and are not intended to limit the scope of the disclosure. The described embodiments comprise different features, not all of which are required in all embodiments of the disclosure. Some embodiments of the present disclosure utilize only some of the features or possible combinations of the features.

Variations of embodiments of the present disclosure that are described, and embodiments of the present disclosure comprising different combinations of features as noted in the described embodiments, will occur to persons with ordinary skill in the art. It will be appreciated by persons with ordinary skill in the art that the present disclosure is not limited by what has been particularly shown and described herein above. Rather the scope of the invention is defined by the appended claims.

In the claims, means-plus-function clauses are intended to cover the structures described herein as performing the recited function and not only structural equivalents, but also equivalent structures. Thus, it is the express intention of the applicant not to invoke 35 USC § 112(f) for any limitations of any of the claims herein, except for those in which the claim expressly uses the words "means for" together with an associated function.

Therefore, although selected aspects have been illustrated and described in detail, it will be understood that various substitutions and alterations may be made therein without departing from the spirit and scope of the present invention, as defined by the following claims.

LIST OF REFERENCE NUMBERS

1 Electrical connection
2 Electrical connection
3 Electrical connection
4 Busbar
5 Coating
6 Power supply
7 Power supply
8 Busbar
9 Busbar
10 Uniform conductive material
11 Uniform conductive material
12 Polymer film
13 Dielectric material
14 Busbar segment
21 Power supply
23 Uniform conductive material
24 Dielectric material
25 Busbar
26 Dielectric space
27 Polymer film
28 Dielectric space
29 Dielectric space
30 Dielectric space
31 Dielectric space
32 Dielectric space
33 Dielectric space
34 Dielectric space
35 Dielectric space
39 Power supply
40 Connection Point
41 Connection Point
42 Connection Point
43 Connection Point
44 Connection Point
45 Connection Point
48 Heating elements
49 Busbar
50 Metal strip
51 Polyester film
52 Busbar
53 Surface/shape
54 Fixture 55 Viewer
56 Uniform conductive material
57 Space
58 Space
59 Dielectric coating
60 Busbar
61 Uniform conductive material
62 Uniform conductive material
63 Voids
$L_x$ Length between busbars
M Unheated or non-contact zone
V Power supply
W Heated or contact zone

What is claimed is:

1. A method for heating of a surface, comprising using conductive continuous busbars and transparent dielectric coatings so as to have an intermittent electrical contact with a conductive film to provide heating,
   wherein the intermittent electrical contact is determined by non-contact spacing M,
   wherein non-contact spacing M used to provide the heating between busbars is determined by the equation $$M = \left(\frac{L_1}{L_2}\right)^2 w - w,$$

where
   $L_1$ is a first linear path across the surfaces between busbars, $L_1$ being the longest vertical path between busbars when busbars are located along a top edge and a bottom edge of the surface,
   $L_2$ is any second linear path across the surface between busbars, $L_2$ being shorter than and parallel to $L_1$, and
   W is the width of a busbar contact region, and
   wherein contact between the conductive film and the electrical busbar is continuous except where a dielectric coating underneath the busbar prevents electrical contact between the busbar and the conductive film.

2. The method of claim 1, wherein the busbars are parallel to each other.

3. The method of claim 1, wherein the busbars are not parallel to each other.

4. The method of claim 1, wherein the conductive film is transparent.

5. The method of claim 1, wherein the dielectric coating is continuous, preventing a continuous busbar over the dielectric coatings from contacting the conductive film except where the busbar protrudes past the dielectric coating making contact.

6. The method of claim 1, wherein each of the busbars are bonded with a conductive adhesive to a copper foil, wherein the respective one of the busbars and the copper foil are laminated together.

7. The method of claim 6, wherein the copper foil is soldered to a power supply.

8. The method of claim 1, using a tapered or decreasing width busbar for uniform resistance heaters.

9. The method of claim 1, for use in constructing intermittent contact busbars for three-dimensional transparent conductive heaters.

10. A method of using varying sheet resistivity to provide heating for heaters with busbars,
    wherein a second sheet resistivity $\rho_2$ is determined using the equation $$\rho_2 = \rho_1 \left(\frac{L1}{L2}\right)^2$$

for the heating, wherein
    $L_1$ is a first linear path across the surfaces between busbars, $L_1$ being the longest vertical path between busbars when busbars are located along a top edge and a bottom edge of the surface,
    $L_2$ is any second linear path across the surface between busbars, $L_2$ being shorter than and parallel to $L_1$, and
    $\rho_1$ is a first sheet resistivity of a conductive film on the heater surface.

11. The method of claim 10, wherein the busbars are parallel to each other.

12. The method of claim 10, further comprising using voids or holes in the conductive heater material to increase sheet resistivity.

13. The method of claim 10, further comprising using conductive dots on the conductive heater material to decrease sheet resistivity.

14. The method of claim 10, further comprising using a combination of conductive dots and voids to give a variation of sheet resistivity.

15. The method of claim 14, wherein the busbars are parallel to each other.

16. A device for manufacturing three-dimensional busbars, wherein the device comprises means for constructing intermittent contact busbars on a three-dimensional transparent conductive heater, wherein the three-dimensional transparent conductive heater comprises the busbars, which are electrically conductive, and dielectric coatings so as to have an intermittent electrical contact with a conductive film, thereby providing heating of the three-dimensional transparent conductive heater,
    wherein the intermittent electrical contact is determined by non-contact spacing M,
    wherein the non-contact spacing M used to provide the heating between busbars is determined by the equation $$M = \left(\frac{L1}{L2}\right)^2 w - w,$$

where
    $L_1$ is a first linear path across the surfaces between busbars, $L_1$ being the longest vertical path between busbars when busbars are located along a top edge and a bottom edge of the surface,
    $L_2$ is any second linear path across the surface between busbars, $L_2$ being shorter than and parallel to $L_1$, and
    W is the width of a busbar contact region, and
    wherein contact between the conductive film and the busbars is continuous except where a dielectric coating underneath the busbars prevents electrical contact between the busbars and the conductive film.

17. Goggles comprising a lens heated using a method for heating of a lens, the method comprising using electrically conductive busbars and dielectric coatings so as to have an intermittent electrical contact with a conductive film coated on a surface of the lens so as to provide heating of the lens,
    wherein the intermittent electrical contact is determined by non-contact spacing M,
    wherein the non-contact spacing M used to provide the heating between busbars is determined by the equation $$M = \left(\frac{L1}{L2}\right)^2 w - w,$$

where
- $L_1$ is a first linear path across the surfaces between busbars, $L_1$ being the longest vertical path between busbars when busbars are located along a top edge and a bottom edge of the surface,
- $L_2$ is any second linear path across the surface between busbars, $L_2$ being shorter than and parallel to $L_1$, and
- W is the width of a busbar contact region, and
- wherein contact between the conductive film and the busbars is continuous except where a dielectric coating underneath the busbars prevents electrical contact between the busbars and the conductive film.

18. A system for providing heating across a transparent or mirrored surface of non-uniform width, comprising:
- a base substrate defining a shape of the surface;
- a thin conductive material applied to the base substrate; and
- busbars applied to the thin conductive material, wherein a first busbar of the busbars is applied to or next to a first edge of the surface and a second busbar of the busbars is applied to or next to a second edge of the surface opposite the first edge,
- wherein the heating is achieved through one of:
  - a dielectric material positioned between the busbars and thin conductive material to enable intermittent contact between the busbars and the thin conductive material; and
  - at least one of holes, voids, and dots applied to the thin conductive material to alter resistivity across a surface defined by the thin conductive material, wherein more of the at least one of holes, voids, and dots are present when the busbars are closer together than when the busbars are farther apart, and
- wherein the intermittent electrical contact is determined by non-contact spacing M,
- wherein the non-contact spacing M used to provide the heating between busbars is determined by the equation $$M = \left(\frac{L1}{L2}\right)^2 w - w,$$

where
- $L_1$ is a first linear path across the surfaces between busbars, $L_1$ being the longest vertical path between busbars when busbars are located along a top edge and a bottom edge of the surface,
- $L_2$ is any second linear path across the surface between busbars, $L_2$ being shorter than and parallel to $L_1$, and
- W is the width of a busbar contact region, and
- wherein contact between the conductive film and the busbars is continuous except where a dielectric coating underneath the busbars prevents electrical contact between the busbars and the conductive film.

19. The system as defined in claim 18, as applied to a heated lens.

20. The system as defined in claim 18, as applied to a heat shield.

* * * * *